United States Patent [19]

Cook

[11] Patent Number: 4,910,997
[45] Date of Patent: Mar. 27, 1990

[54] FLUCTUATING STRESS GENERATING APPARATUS AND METHOD

[75] Inventor: Nicholas J. Cook, St. Albans, England

[73] Assignee: The Secretary of State of the Environment, London, England

[21] Appl. No.: 303,673
[22] PCT Filed: Aug. 6, 1987
[86] PCT No.: PCT/GB87/00556
§ 371 Date: Jan. 24, 1989
§ 102(e) Date: Jan. 24, 1989
[87] PCT Pub. No.: WO88/01051
PCT Pub. Date: Feb. 11, 1988

[30] Foreign Application Priority Data

Aug. 7, 1986 [GB] United Kingdom ............... 8619295

[51] Int. Cl.$^4$ ............................................. G01M 3/02
[52] U.S. Cl. ......................................... 73/37; 73/807
[58] Field of Search .............. 73/786, 806, 807, 865.6, 73/866, 37, 40

[56] References Cited

U.S. PATENT DOCUMENTS

| 2,345,387 | 3/1944 | Elsey | 73/40 |
| 2,694,924 | 11/1954 | Matlock et al. | 73/807 |
| 2,826,910 | 3/1958 | Bell et al. | |
| 3,332,281 | 7/1965 | Spangler | 73/807 |
| 4,517,826 | 5/1985 | Cole et al. | 73/40 |
| 4,635,469 | 1/1987 | Modera et al. | 73/40 |

FOREIGN PATENT DOCUMENTS

| 696324 | 11/1979 | U.S.S.R. | 73/40 |
| 770550 | 3/1957 | United Kingdom | |

OTHER PUBLICATIONS

Research Disclosure, No. 244, Aug. 1984, (Havant, Hampshire, GB) Automatic Wind–Uplift, p. 387, by K. R. Johnson.

Primary Examiner—Hezron E. Williams
Attorney, Agent, or Firm—Nixon & Vanderhye

[57] ABSTRACT

Apparatus for applying a fluctuating stress to, for example, a gable end of a house includes a pressure enclosure. An air compressor is connected to the pressure enclosure via a series of gauged valves whose positions are continuously variable between limiting positions where the air compressor supplies all its output to, or takes all its output from the pressure enclosure. The effects of gusty winds can thus be simulated.

10 Claims, 5 Drawing Sheets

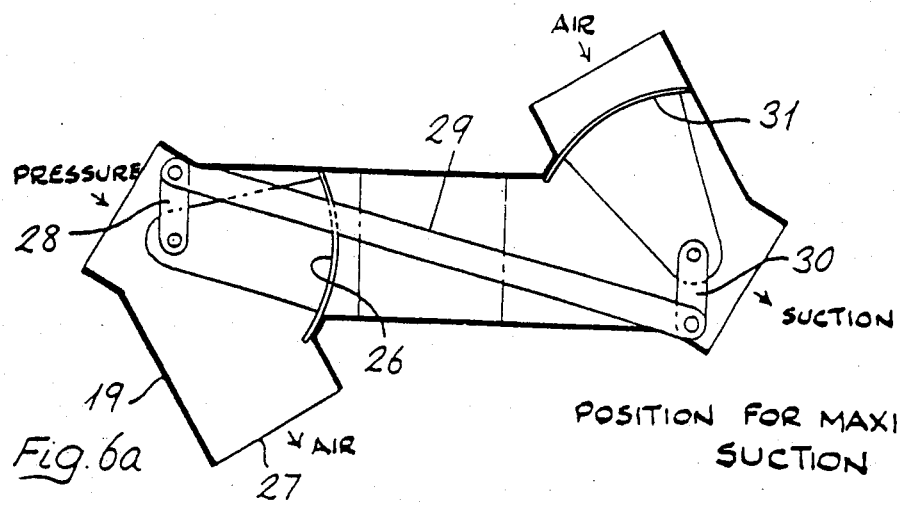
Fig. 6a — POSITION FOR MAXIMUM SUCTION
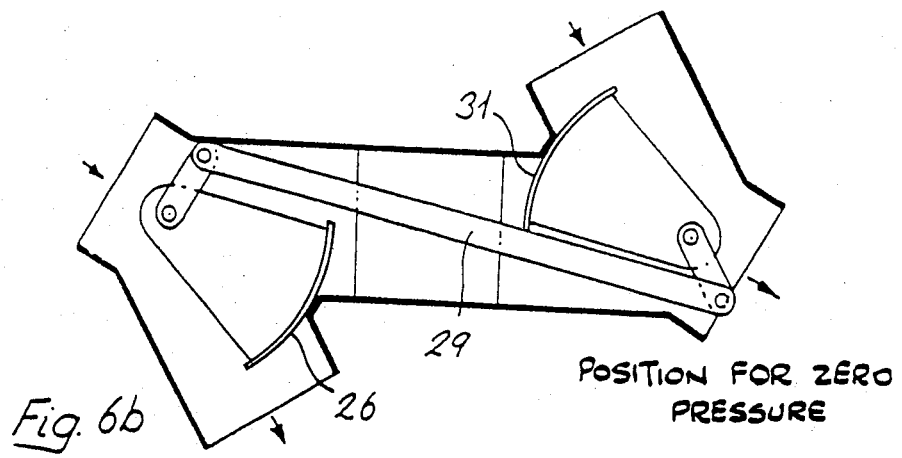
Fig. 6b — POSITION FOR ZERO PRESSURE
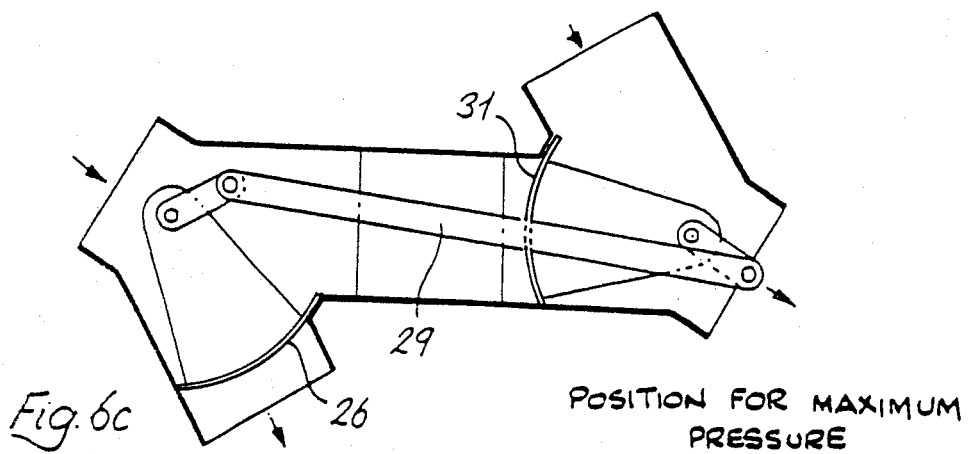
Fig. 6c — POSITION FOR MAXIMUM PRESSURE

FLUCTUATING STRESS GENERATING APPARATUS AND METHOD

BACKGROUND OF THE INVENTION

This invention relates to testing apparatus and a method of testing using such apparatus. In particular, it relates to apparatus usable in the testing of buildings under wind stress.

In the testing of buildings, a uniformly distributed load can be applied on to a horizontal test surface by weights or sand, provided there is no need to change the load quickly. However if an upward load is required, the test surface is not horizontal, or the load is to be varied quickly (to stimulate wind effects, for example), it becomes impractical to generate proof loads in this way. Apparatus has therefore been devised in which a pair of co-operating valves may be coupled to an air circulating system to produce a rapidly fluctuating stress system.

SUMMARY OF THE INVENTION

According to one aspect of the present invention an apparatus for applying a fluctuating stress includes means for defining a pressure enclosure and air compression means having an intake and an outlet characterised by a control valve assembly connecting the pressure enclosure to the air compression means, the control valve assembly being provided with movable valve members continuously adjustable between first positions where the intake is connected to the pressure enclosure and the outlet is connected to atmosphere and second positions where the intake is connected to atmosphere and the outlet is connected to the pressure enclosure through intermediate positions where both intake and outlet are connected partly to atmosphere and partly to the pressure enclosure.

An embodiment of the invention consists of apparatus for applying a fluctuating stress including means for defining a pressure enclosure and air compression means characterised by the means to compress air having an inlet port and an outlet port, first conduit means to conduct air from the outlet port, second conduit means to conduct air to the inlet port, first valve means having an inlet port connected to the first conduit means and having a pair of outlet ports together with adjustable valve members to divert air from a first to a second of its outlet ports, second valve means connected to the second conduit means and having a pair of inlet ports together with adjustable valve members to control relative opening of its first and second inlet ports and an outlet port connected to the second conduit means, coupling means to couple the adjustable valve members of the valve means, third conduit means connected to one outlet port of the first valve means and one inlet port of the second valve means, the third conduit means having a port which is connectable to means defining a pressure enclosure whereby air pressure therein may be varied.

According to another aspect of the invention a method of testing a structure by applying fluctuating stress thereto includes steps of defining a pressure enclosure abutting the structure, connecting to the pressure enclosure air compression means having an intake and an outlet and characterised by the fluctuating stress being applied by varying the pressure in the pressure enclosure by operating a control valve assembly connecting the pressure enclosure to the air compression means, operation of the control valve assembly varying the positions of the movable valve members continuously between first positions connecting the intake to the pressure enclosure and the outlet to atmosphere and second positions connecting the intake to atmosphere and the outlet to the pressure enclosure through intermediate positions connecting both intake and outlet partly to atmosphere and partly to the pressure enclosure.

The movable valve members are preferably adjustable under computer controlled means whereby pressure within the pressure enclosure is varied according to a program which may be predetermined or random.

BRIEF DESCRIPTION OF THE DRAWINGS

An embodiment of the invention will now be described by way of example with reference to the accompanying drawings in which:

FIG. 6a to c is an explanatory diagram for different air flow conditions.

DETAILED DESCRIPTION OF THE PREFERRED EMBODIMENT

Figure 1:
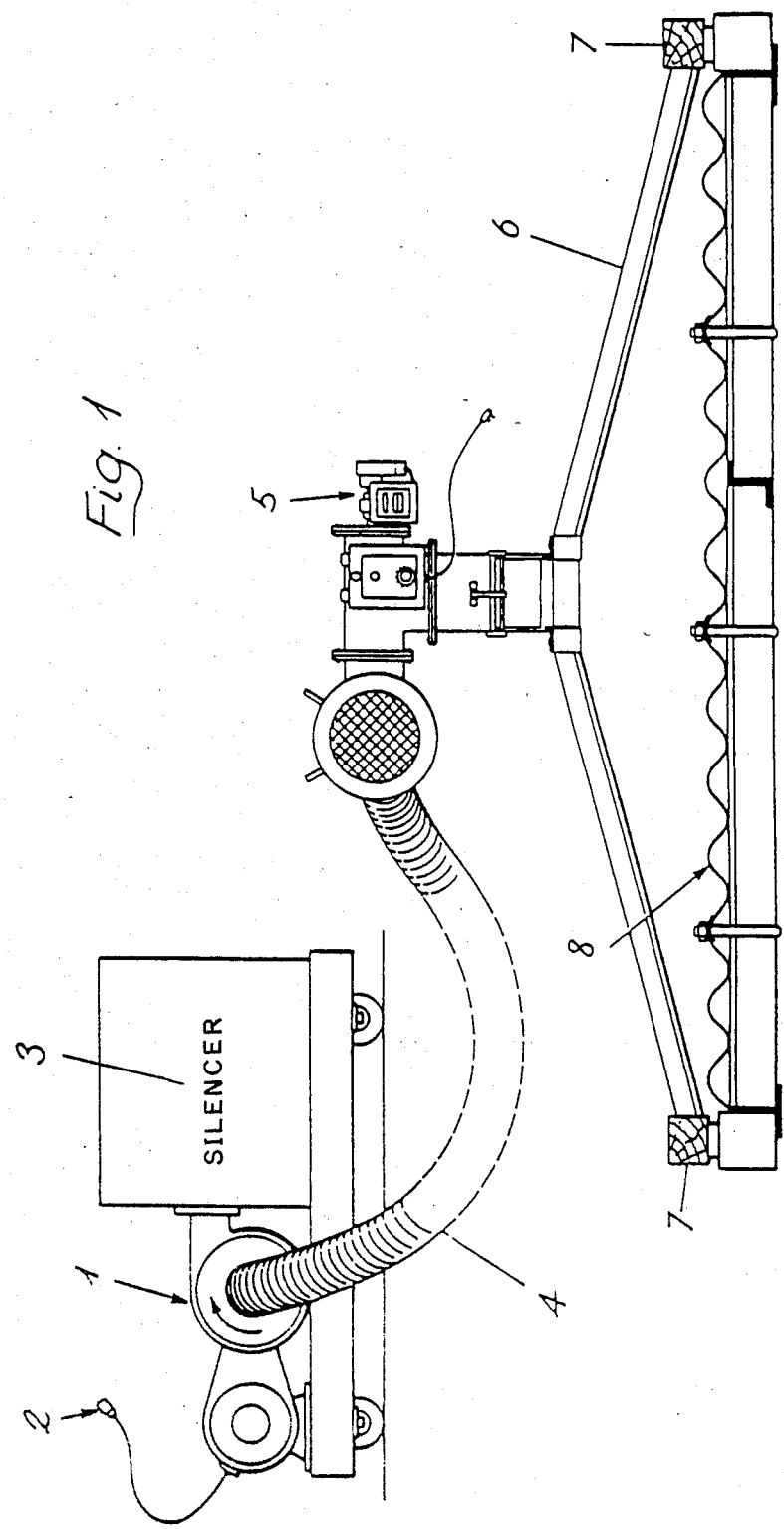
FIG. 1 shows the general assembly of a test rig.
Figure 2:
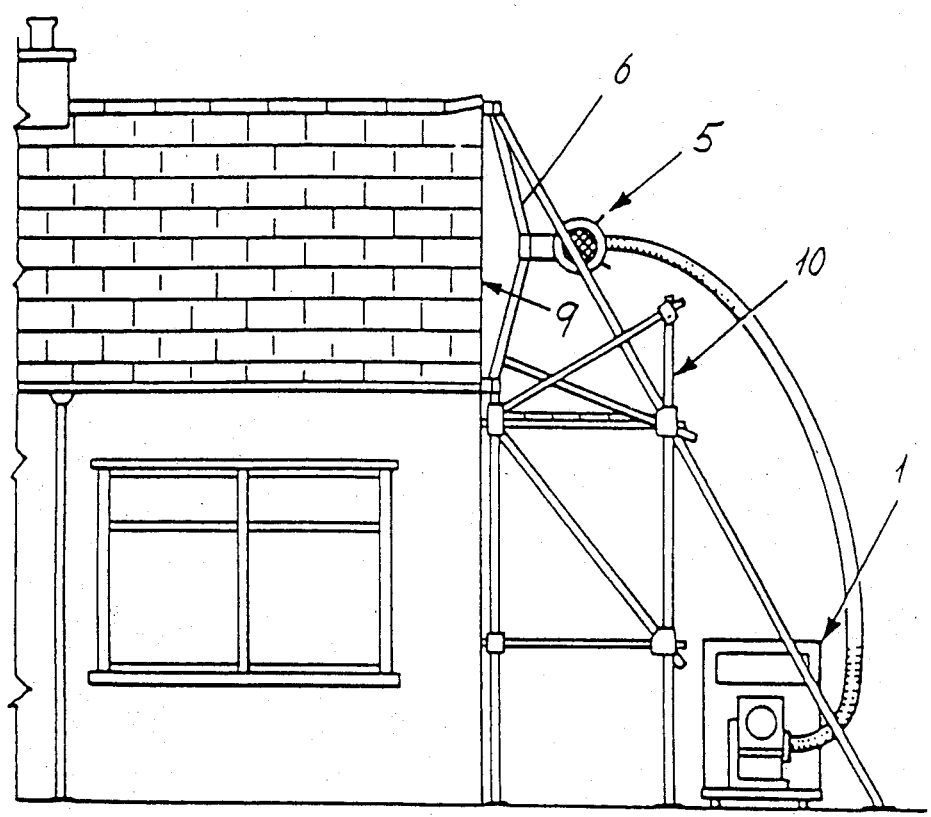
FIG. 2 shows a method of testing in which the test rig of FIG. 1 is applied to a house.

Referring now to the drawings, a test rig for applying a fluctuating stress to a building comprises motor driven fan 1 with power supply 2 and silencer 3 coupled by means of a flexible hose 4 to a control valve assembly 5. Directly coupled to the control valve assembly is a pressure containment cover 6 with seats 7 to couple it to a system under test 8. In use the test rig is attached to the system under test such as the gable end 9 of a house such that the cover 6, seats 7 and end 9 form a pressure enclosure abutting the structure (FIG. 2). It may be held in position by support scaffolding 10.

Figure 3:
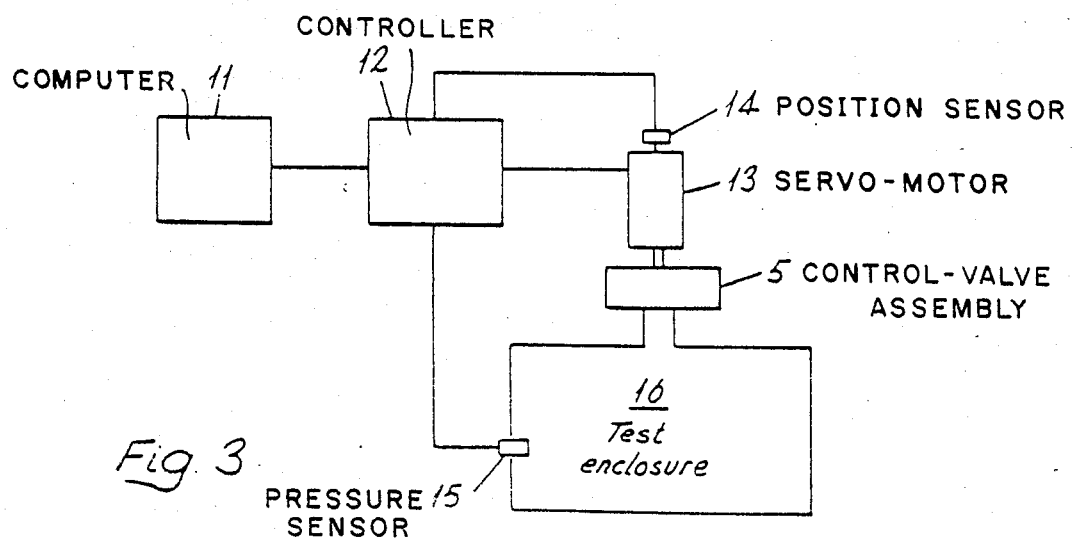
FIG. 3 is a block diagram of a control system for use with the test rig.

The control system for the control valve assembly 5 (FIG. 3) comprises a computer 11 coupled to an electronic controller 12 for a servo-motor 13 attached to the air supply control valve assembly 5. A position sensor 14 on the servo-motor and a pressure sensor 15 linked to the test enclosure 16 provide feedback to the electronic controller.

Figure 4:
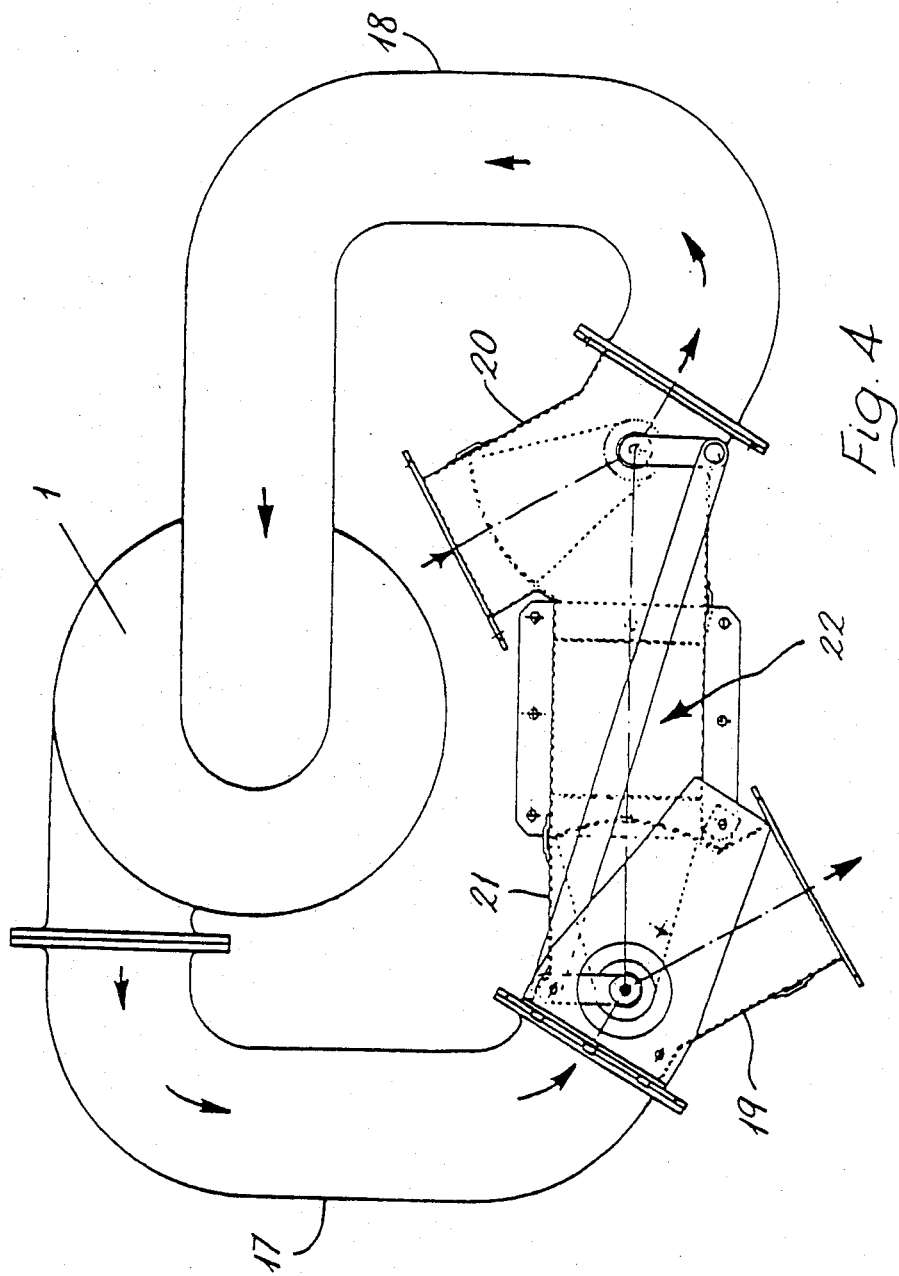
FIG. 4 is an assembly of control valves and air pump incorporated in the test rig.

The controlling air flow is generated by a fan 1 (FIG. 4) having an output conduit 17 and an input conduit 18 consisting of flexible hoses. The output conduit is coupled to the inlet port of a first valve 19 of the control valve assembly. The input conduit is coupled to the output port of a second valve 20 of the control valve assembly. The valves are linked by a third conduit 21 having an output port 22 to the pressure enclosure.

Figure 5:
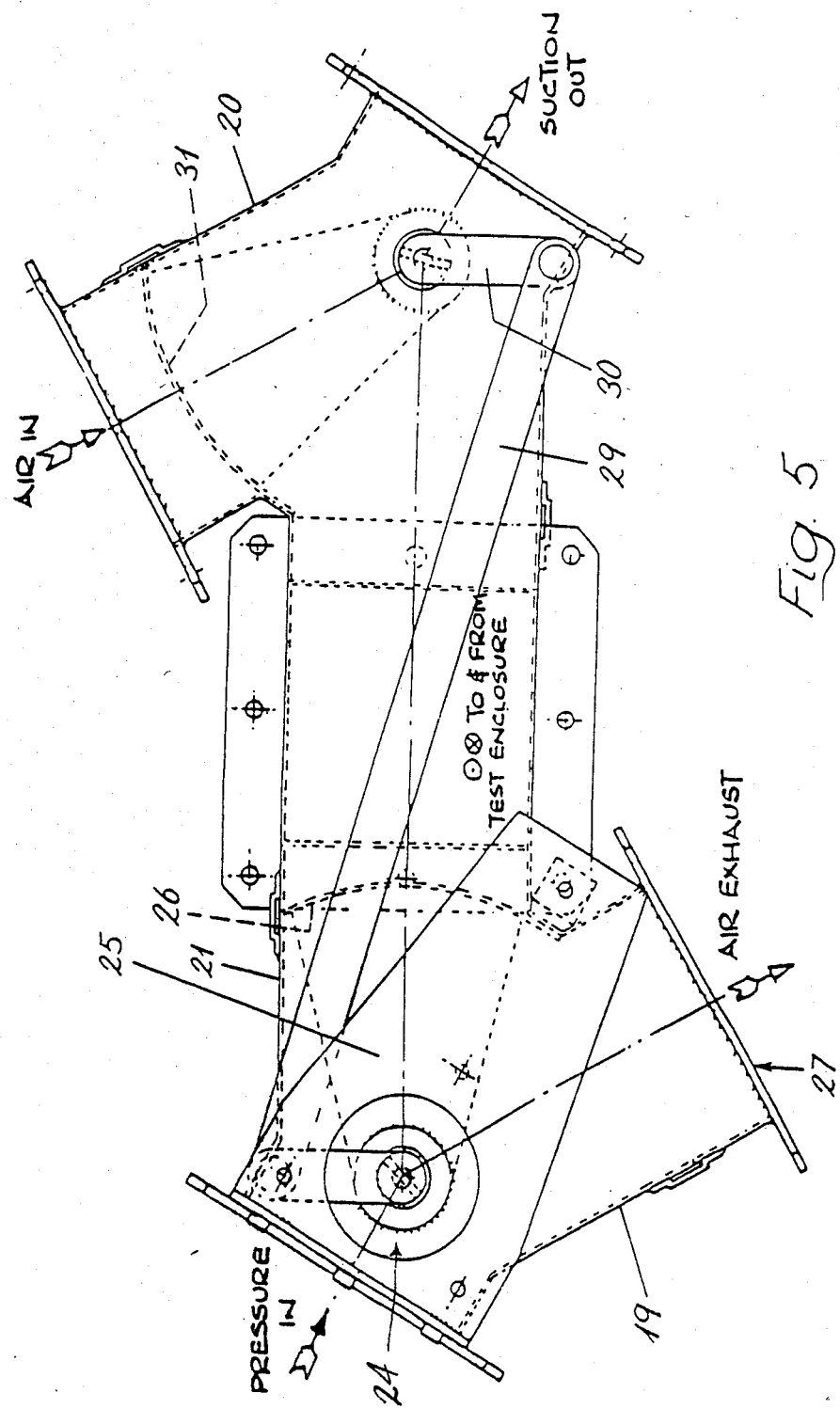
FIG. 5 is a more detailed diagram showing the mechanical arrangement of the control valves of FIG. 4.

The control valve assembly (FIG. 5) comprises a first valve 19 with a control motor 24 mounted on a mounting plate 25 to control a gate valve member 26 which is continuously adjustable to divert air flow from the outlet connected to conduit 21 to an exhaust port 27. The gate valve member 26 is coupled by a system of cranks 28–30 to a gate valve member 31 on a second valve 20 so that air may be taken in a continuously adjustable manner either from the atmosphere or from the third conduit 21.

With this apparatus the desired pressure is stored as a file in a portable computer (not shown). The computer reads the pressure in the pressure enclosure every 25 mS and issues instructions to the servo-motor which adjusts the valve until this test pressure coincides with the filed record.

Other operational procedures, such as a random variation of the pressure by the computer 11, will readily be apparent. With random generation a record of the pressure fluctuations may be kept on the portable computer or on computer 11. Positions of valve members 26,31 for maximum suction (minimum pressure), ambient pressure (zero pressure differential) and maximum pressure are shown in FIGS. 6a, 6b and 6c, respectively.

What is claimed is:

1. Apparatus for applying a fluctuating stress including means for defining a pressure enclosure and air compression means having an intake and an outlet, characterised by a control valve assembly connecting the pressure enclosure to the air compression means, the control valve assembly being provided with movable valve members continuously adjustable between first positions where the intake is connected to the pressure enclosure and the outlet is connected to atmosphere and second positions where the intake is connected to atmosphere and the outlet is connected to the pressure enclosure, through intermediate positions where both intake and outlet are connected partly to atmosphere and partly to the pressure enclosure.

2. Apparatus as claimed in claim 1 comprising means defining a pressure enclosure characterised by a pressure containment cover and seats whereby in use the pressure enclosure is defined between the cover, the seats and a surface to which the fluctuating stress is applied.

3. Apparatus for applying a fluctuating stress including means for defining a pressure enclosure and air compression means characterised by the means to compress air having an inlet port and and outlet port, first conduit means to conduct air from the outlet port, second conduit means to conduct air to the inlet port, first valve means having an inlet port connected to the first conduit means and having a pair of outlet ports together with adjustable valve member to divert air from a first to a second of its outlet ports, second valve means connected to the second conduit means and having a pair of inlet ports together with adjustable valve member to control relative opening of its first and second inlet ports and an outlet port connected to the second conduit means, coupling means to couple the adjustable valve members of the valve means, third conduit means connected to one outlet port of the first valve means and one inlet port of the second valve means, the third conduit means having a port which is connectable to means defining a pressure enclosure whereby air pressure therein may be varied.

4. Apparatus as claimed in claim 1 characterised by movable valve members controlled by computer operated means.

5. Apparatus as claimed in claim 4 characterised by movable valve members controlled according to a predetermined program.

6. Apparatus as claimed in claim 4 characterised by movable valve members controlled according to a random program.

7. A method of testing a structure by applying fluctuating stress thereto including steps of defining a pressure enclosure abutting the structure, connecting to the pressure enclosure a air compression means having an intake and an outlet and characterised by the fluctuating stress being applied by varying the pressure in the pressure enclosure by operating a control valve assembly connecting the pressure enclosure to the air compression means, operation of the control valve assembly varying the positions of movable valve members continuously between first positions connecting the intake to the pressure enclosure and the outlet to atmosphere and second positions connecting the intake to atmosphere and the outlet to the pressure enclosure through intermediate positions connecting both intake and outlet partly to atmosphere and partly to the pressure enclosure.

8. Apparatus as claimed in claim 3 including computer operated means whereby the positions of the valve means are varied.

9. Apparatus as claimed in claim 8 whereby the positions of the valve means are varied according to a predetermined program.

10. Apparatus as claimed in claim 8 whereby the positions of the valve means are varied according to a random program.

* * * * *